United States Patent
Chen et al.

(10) Patent No.: US 12,352,760 B2
(45) Date of Patent: Jul. 8, 2025

(54) PROTEIN SCAFFOLD CAPABLE OF CARRYING RADIOACTIVE SIGNALS AND APPLICATION IN ANTIBODY DETECTION

(71) Applicant: JIANGSU PROVINCE HOSPITAL THE FIRST AFFILIATED HOSPITAL WITH NANJING MEDICAL UNIVERSITY, Jiangsu (CN)

(72) Inventors: Heng Chen, Jiangsu (CN); Tao Yang, Jiangsu (CN); Yong Gu, Jiangsu (CN)

(73) Assignee: JIANGSU PROVINCE HOSPITAL THE FIRST AFFILIATED HOSPITAL WITH NANJING MEDICAL UNIVERSITY, Jiangsu (CN)

( * ) Notice: Subject to any disclaimer, the term of this patent is extended or adjusted under 35 U.S.C. 154(b) by 0 days.

(21) Appl. No.: 18/829,320

(22) Filed: Sep. 10, 2024

(65) Prior Publication Data
US 2025/0085294 A1    Mar. 13, 2025

(30) Foreign Application Priority Data
Sep. 11, 2023   (CN) .......................... 202311164317.4

(51) Int. Cl.
G01N 33/68 (2006.01)
C07K 14/00 (2006.01)
G01N 33/60 (2006.01)

(52) U.S. Cl.
CPC ....... *G01N 33/6854* (2013.01); *C07K 14/001* (2013.01); *G01N 33/60* (2013.01)

(58) Field of Classification Search
None
See application file for complete search history.

(56) References Cited

PUBLICATIONS

Calabretta et al. The effect of RNA base lesions on mRNA translation. Nucleic Acids Res. May 19, 2015;43(9):4713-20. (Year: 2015).*

* cited by examiner

*Primary Examiner* — Rebecca M Giere
*Assistant Examiner* — Alexander Alexandrovic Volkov
(74) *Attorney, Agent, or Firm* — JC ONE WORLD

(57) ABSTRACT

A protein scaffold capable of carrying radioactive signals and application thereof in antibody detection are provided. The present disclosure successfully finds out a protein scaffold R12 capable of carrying radioactive signals, which is used for assisting part of antigens to capture corresponding antibodies; and because the method is used for carrying signals and eliminating more severe screening conditions of cross reaction in the screening process, the method is not limited to the method in application, and the method can be directly used for a technical platform which only needs to eliminate the cross reaction.

2 Claims, 5 Drawing Sheets
Specification includes a Sequence Listing.

PROTEIN SCAFFOLD CAPABLE OF CARRYING RADIOACTIVE SIGNALS AND APPLICATION IN ANTIBODY DETECTION

CROSS-REFERENCE TO RELATED APPLICATION

This application claims the priority benefit of China application serial no. 202311164317.4, filed on Sep. 11, 2023. The entirety of the above-mentioned patent application is hereby incorporated by reference herein and made a part of this specification.

REFERENCE TO A SEQUENCE LISTING

The instant application contains a Sequencing Listing which has been submitted electronically in XML file and is hereby incorporated by reference in its entirety. Said XML copy, created on Sep. 5, 2024, is named 148725-US-Sequence Listing and is 19,176 bytes in size.

BACKGROUND

Technical Field

The present disclosure belongs to the technical field of biological medicines, and specifically relates to a protein scaffold Ruber12 capable of carrying radioactive signals and application in antibody detection.

Description of Related Art

The radioligand binding assay (RBA) detection platform obtains radioactive protein antigens by adding radioactive amino acid raw materials (such as $S^{35}$ labeled methionine) during the rapid transcription and translation process of plasmids. The principle of in situ substitution of amino acids won't change the obtained protein spatial structures, which can maintain high specificity of the results. And as an open technical platform, the radioligand binding assay (RBA) detection platform has a wide detection range and a strong sensitivity, and can obtain enough antigen raw materials within 90 minutes. Thanks to the above characteristics, this technology is widely used in the capture of cutting-edge antibodies. The application premise of the detection platform is that the protein sequence to be translated contains a certain methionine sequence itself (generally not less than 8 in order to ensure the signal carrying efficiency and facilitate batch detection) and is used for being replaced by the radioactive methionine, but in the practical research process, the inventor found that many antigens do not contain methionine itself and can not carry radioactive signals, which can not be applied to the method for capturing corresponding antibodies, so that the application of RBA is limited to a certain extent.

SUMMARY

One objective of the present disclosure is to provide a protein scaffold capable of carrying radioactive signals, which has an amino acid sequence as follows:

(SEQ ID NO: 12)
IKNILQPGSVDSQTEMVLVNAVYFKGMWEKAFKDEDTQAMPFRMTEQES

TPVQMMYQVGSFKVAEMASEKMKILELPYASGELSMLVLLPDDVSGLEE

-continued

IENAITFEKLTEWTSSSIMEERKIKVYLPRMKMEEKYNLTSVLMALGMT

DLF.

Another objective of the present disclosure is to provide an application of the protein scaffold in preparing antibody detection products.

Further, the antibody detection products are used for a radioligand binding assay method.

Furthermore, after the protein scaffold gene sequence is connected with an antigen gene sequence, an antigen protein carrying radioactive signals can be obtained through a transcription and translation and is used for detecting antibodies by the radioligand binding assay method.

Yet another objective of the present disclosure is to provide a detection kit for an anti-butyrophilin 3A1 antibody. The detection kit includes a radioactive antigen protein AR12A, the radioactive antigen protein AR12A is obtained by labeling the antigen protein AR12A with $S^{35}$-methionine, and a gene sequence of the antigen protein AR12A includes a gene sequence of the protein scaffold and two sections of gene sequences of the anti-butyrophilin 3A1.

In one embodiment of the present disclosure, target genes (two sections of BTN3A1 genes are connected to two ends of a No. 12 protein scaffold R12 through hinge genes) are introduced into a Vector pTnT™ Vector to construct an AR12A plasmid, and then the plasmid is rapidly transcribed and translated to obtain radiolabeled antigen proteins. Specifically, the plasmid structure includes: xhoI (ctcgag)+kozak sequence (gccacc)+ATG+target sequence+stop codon+XbaI. Each radioactive antigen protein AR12A obtained after transcription and translation includes two BTN3A1 protein antigen structure domains, the intermediate of the two BTN3A1 protein antigen structure domains is connected with each other through a hinge protein, the capacity of the radioactive antigen protein for carrying radioactive signals is effectively doubled, and the capacity of the radioactive antigen protein for capturing antibodies is greatly improved through the two antigen structure domains.

Further, the detection kit further includes a TBST buffer solution, a protein A agarose, a protein G agarose, a positive control and a negative control.

The present disclosure successfully finds out a protein scaffold R12 capable of carrying radioactive signals, which is used for assisting part of antigens to capture corresponding antibodies; and, due to the more stringent screening conditions of carrying signals and eliminating cross reactions during the screening process, the application of the protein scaffold R12 will not be limited to this methodology, and the protein scaffold R12, can also be directly used for technology platforms that only require the elimination of cross reactions.

BRIEF DESCRIPTION OF THE DRAWINGS

FIG. 1 illustrates results of expression profilings on 56 human tissues and human islets in a GTEx database and a Tiger database.

FIG. 2 illustrates results of analyses on BTN3A1 gene expression level by using a GEO database and a nPOD database.

FIG. 3 illustrates results of plasmid transcription efficiency of alternative protein scaffolds No. 1-18.

FIG. 4 illustrates a schematic diagram of an antigenic protein AR12A.

FIG. 5 illustrates radiation readings of a BTN3A1A detection at various simulated sample additions.

DESCRIPTION OF THE EMBODIMENTS

Figure 1:

In order to solve the problem that some antigen cannot carry a radioactive signal in RBA detection, the inventor designs and searches some methionine-rich gene sequences which are far away from human species and are derived from rare animals, and can be used as scaffold proteins after transcription and translation, and the characteristics of 1) it can carry the radioactive signal and 2) it has no cross-reactivity with various samples. The antigen can be applied to RBA by utilizing the radioactive signal carried by the protein scaffolds to capture corresponding antibodies. The inventor finds 43 gene sequences which are rich in methionine and are derived from different animals through screening thousands of genes in a gene library, then calculates the methionine sequence content, and excludes 25 sequences with lower content; subsequently, performs the plasmid synthesis on the remaining 18 gene sequences. Through experiments, the followings are verified: (1) the transcriptional translation efficiency of these 18 protein scaffolds; (2) the cross reaction of healthy human serum (because of the possible homology between scaffold proteins and proteins in some human food, in order to avoid non-specific binding of antibodies in human serum to scaffold proteins used in the assay caused by food allergy, scaffold proteins that may have this problem will be excluded by reaction with normal human serum); (3) the cross reaction of serum of metabolic patients (because the microenvironment in metabolic patients is different from that of normal human, there may be some metabolic molecules affecting the detection on specificity, and scaffold proteins that may be disturbed by such microenvironment are further excluded herein).

In the experiment, the sequences with transcription and translation failure and cross reaction are removed, the remaining gene sequence is from the *Phoenicopterus ruber*, the gene name N337-12018 which is rich in methionine, the protein is taken as a scaffold protein, the protein is named as R12, and the protein is applied to capturing of a new antibody.

To verify the effectiveness of the screened protein scaffold R12, the protein scaffold R12 is further applied to the detection of antibodies against the butyrophilin BTN3A1 (Butyrophilin A1, BTN3 A1). The inventors found that BTN3A1 is associated with diabetes in earlier GWAS studies, suggesting that diabetics may have antibodies to the protein, and no RBA detection method for BTN3A1 autoantibodies is currently available. By evaluating the structure of the BTN3A1 protein, the methionine content is extremely low, and the sequence of the target antigen only includes 4 methionine, so that the detection requirement is not satisfied enough when the target antigen carries radioactive signals on its own. Thus a protein scaffold for carrying radioactive signals is introduced to assist in detection of the antibody. Specifically, the target gene sequence is connected to two sides of a protein scaffold R12 through a hinge gene to construct corresponding plasmids, the radioactive antigen proteins obtained after transcription and translation can effectively carry radioactive signals, each protein contains two identical antigen structure domains, and the capacity of capturing antibodies is directly doubled.

The specific experimental method includes the following steps:

1. Gene screening: 18 gene sequences rich in methionine which are far away from human species and derived from rare animals are finally determined by continuously screening and comparing thousands of potential gene sequences in a gene library, the gene sequences are used as protein scaffold sequences to be selected.
2. Plasmid construction: the 18 selected gene sequences are inserted into Vector pTnT™ Vector and 18 plasmids are constructed.
3. Transcription and translation of plasmids: the existing radioligand binding assay method (RBA) detection platform in the inventor's laboratory is used for rapidly transcribing and translating plasmids in vitro to obtain 18 radioactive proteins, 7 plasmids with extremely low transcription and translation efficiency are removed, and the remaining 11 protein scaffold sequences to be selected and the corresponding radioactive proteins are left.
4. Cross-reaction of scaffold proteins with normal human serum: because of the possible homology between the scaffold proteins and proteins in some human food, the inventors design to exclude scaffold proteins that may have this problem by reacting with normal human serum in order to avoid non-specific binding of antibodies in human serum with scaffold proteins used in the assay caused by food allergy. The remaining 11 candidate radioactive proteins are incubated with normal human serum, unbound radioactive proteins are removed by repeated washing, the radioactivity intensity of the remaining complex is read, and 7 scaffold proteins with certain cross reaction with normal human serum are excluded.
5. Cross-reaction of scaffold proteins with serum of metabolic patients: because the microenvironment in metabolic patients is different from that of normal human, there may be some metabolic molecules affecting the specificity of the detection, and the inventors herein will further exclude scaffold proteins that may be disturbed by such microenvironment. The remaining 4 scaffold proteins in above 4 are incubated with serum samples of metabolic patients according to the experimental procedure, and 3 scaffold proteins with certain cross reaction with serum of metabolic patients are removed. Because of higher transcription and translation efficiency and low background, the No. 12 (Ruber, R12) is preliminarily selected as a protein scaffold which is to be adopted and carries radioactive signals, and to assist subsequent antigens in the capture of corresponding antibodies.
6. Application of protein scaffold R12 in detection of anti-butyrophilin 3A1 (BTN3A1) antibody (BTN3A1A)
   a. Plasmid construction: A plasmid BTN3A1R12BTN3A1 (AR 12A) which simultaneously includes a protein scaffold R12 gene sequence and two BTN3A1 gene sequences is constructed.
   b. The corresponding radioactive antigen protein AR12A is obtained by using the existing radioligand binding assay method (RBA) detection platform in the laboratory of the inventor to rapidly transcribe and translate plasmids in vitro. The commercial antibody BTN3 A1A purchased directly is taken as a simulated sample to be combined with the radioactive antigen protein AR 12A obtained through transcription and translation, and the effectiveness of the AR12A protein as well as the experimental flow and the efficiency of carrying radioactive signals are identified.

c. The sample to be detected is reacted and combined with the radioactive antigen protein AR12A, the unbound radioactive antigen is removed through a sufficient washing, the radioactivity intensity of the remaining antigen-antibody complex is read, and the content index of the antibody in the sample is calculated. The differences of BTN3A1A detection results are statistically compared among different sample types.

d. Part of positive samples are selected to perform competitive inhibition experiments with purchased commercial antigen proteins without radioactive signals to verify the authenticity of the results.

Based on the searching and verification of the above experiments, the present disclosure successfully finds the protein scaffold R12 which can carry radioactive signals and is used for assisting part of antigens to capture corresponding antibodies; and because of more severe screening conditions of carrying signals and eliminating cross reaction during the screening process of the protein scaffold R12, the application of the protein scaffold R12 is not be limited to this methodology, and the protein scaffold R12 can also be directly used for a technical platform which only require to eliminate the cross reaction.

Preferred implementations of the present disclosure will be described in detail below with reference to examples. It should be understood that the following examples are given for illustrative purposes only and are not intended to limit the scope of the present disclosure. Various modifications and alterations of present disclosure may be made by those skilled in the art without departing from the spirit and scope of present disclosure.

The experimental methods used in the following examples are conventional methods unless otherwise specified.

Materials, reagents and the like used in the examples described below are commercially available unless otherwise specified.

The experimental materials used in the following examples are as follows:

1. Sample source: the detection of positive quality by BTN3A1A comes from purchased commercial antibodies. Negative quality control serum specimens are obtained from healthy volunteers without a family history of diabetes. There are 643 cases of type 1 diabetes (T1DM) and 404 cases of non type 1 diabetes (non-T1DM) in the serum of diabetic patients (DM). 382 healthy population from the recruited group [age (33.5±5.3) years old; 190 male and 192 female]; the results of oral glucose tolerance test (OGTT) fasting and 2 h blood glucose are normal, excluding heart, brain, liver, kidney and other chronic and endocrine diseases, no family history of diabetes and autoimmune disease history.

2. Main reagents and instruments: TNT SP6 rapid transcription translation kit (L2080, Promega); $s^{35}$-methionine (NEG 709A 5 mCi, PerkinElmer); protein A agarose PA (17-5280-02, GE); protein G agarose PG (17061805, GE); 96-well PVDF plates (3504, Corning); Microscint-20 scintillation solution (6013621, PerkinElmer); TBST buffer (Tris-Base 2.424 g, NaCl 8.70 g, Tween-20 1.5 mL, BSA 1.0 g plus distilled water to 1000 mL, pH 7.4); β Counter Liquid Scintillation Counter (2450 Microplate Counter, Perkin-Elmer); Protein purification column NAP Column (17-0853-02, GE); BTN3A1 (Ag 18114, proteintech); BTN3A1A (25221-1-AP, proteintech); plasmid Vector pTnT™ Vector (L5610, Promega).

Example 1

It is revealed through the analysis of the expression profiles on 56 human tissues and human islets in the GTEx (Genotype-Tissue Expression) database and the Tiger (Tumor Immunotherapy Gene Expression Resource) database that the BTN3A1 gene is expressed in higher abundance as a broad-spectrum expressed gene in islets and pancreatic tissues, as illustrated in FIG. 1.

Figure 2:
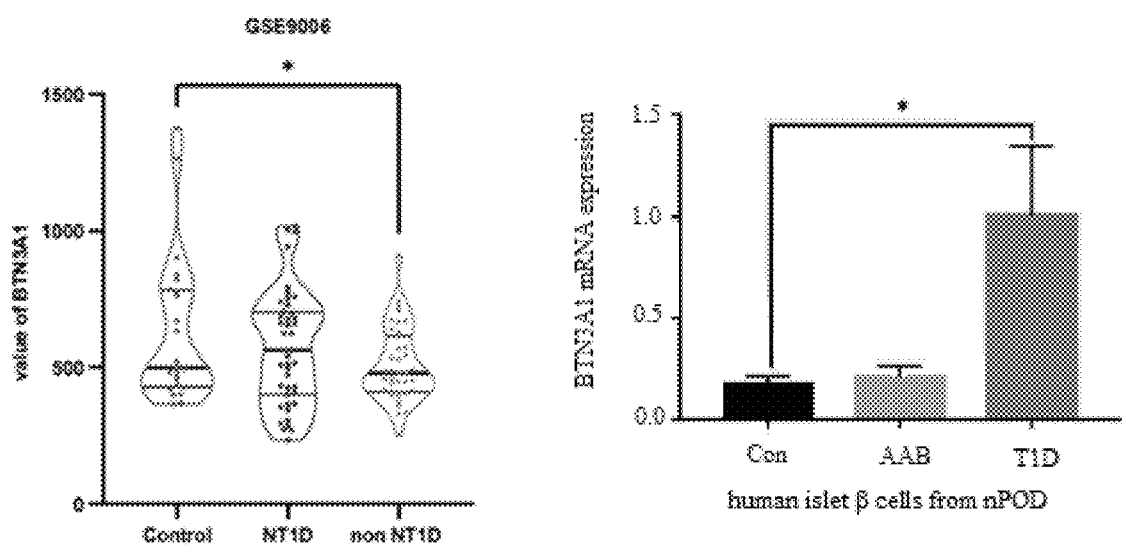

In the GEO (Gene Expression Omnibus) database, it is found through the analysis that the expression of BTN3A1 gene in peripheral blood of non-new-onset T1D patients decreases. As illustrated in the left figure of FIG. 2 (NTID is new-onset-type 1 diabetes, nonNTID is non-neo-type 1 diabetes). In the analysis of the Network for Pancreatic Donors with Diabetes (nPOD), it is found that the expression amount of the gene is significantly up-regulated in the single cell sequencing of islet B cells in T1DM patients, as illustrated in the right figure in FIG. 2 (AAB is an autoantibody-positive uninfected population sample).

Further, the analysis of the Bioinformatics Epitope Prediction shows that the protein encoded by the gene contains a plurality of potential islet antigen-specific epitope polypeptides, which suggests that the protein encoded by the gene is a potential islet-specific autoantigen, as shown in Table 1.

TABLE 1

| HLA-A0201 list of restricted epitope polypeptides | | | | | | | |
|---|---|---|---|---|---|---|---|
| allele | seq_num | start | end | length | peptide | score | percentile_rank |
| HLA-A*02:01 | 5 | 11 | 19 | 9 | ALAGTLPVL (SEQ ID NO: 20) | 0.872816 | 0.05 |
| HLA-A*02:01 | 1 | 2 | 10 | 9 | KMASFLAFL (SEQ ID NO: 21) | 0.744097 | 0.11 |
| HLA-A*02:01 | 4 | 20 | 28 | 9 | GLYAVAASV (SEQ ID NO: 22) | 0.702861 | 0.13 |

TABLE 1-continued

HLA-A0201 list of restricted epitope polypeptides

| allele | seq_num | start | end | length | peptide | score | percentile_rank |
|---|---|---|---|---|---|---|---|
| HLA-A*02:01 | 9 | 5 | 13 | 9 | FLDVSFSEA (SEQ ID NO: 23) | 0.664453 | 0.15 |
| HLA-A*02:01 | 8 | 32 | 40 | 9 | KLPKPPKKV (SEQ ID NO: 24) | 0.544369 | 0.24 |

It is therefore presumed that islet-specific autoantibodies against BTN3A1 may be present in type 1 diabetics.

Example 1 Screening of Scaffolds

1. Plasmid Construction Plan

After the codon optimization according to the mammalian protein expression system (avoiding two enzyme cleavage sites), the plasmid is constructed on the plasmid vector pTnT™ Vector (L5610, Promega), including kozak sequence, XhoI and XbaI enzyme cleavage sites, and the target sequence.

The plasmid structure includes: XhoI (ctcgag)+kozak sequence (gccacc)+ATG+target sequence+stop codon+XbaI.

The 18 protein scaffold sequences from rare animals to be selected are used as target sequences to be inserted into the above-mentioned carrier, to construct the corresponding 18 plasmids.

The amino acid sequences of the protein scaffolds 1 to 18 to be selected are as follows.

No. 1: N306_04127
(SEQ ID NO. 1)
AIYFKGMWQKAFKDEDTQEVPFRMTEQQSKPVQMMYQTGSFKVAVVASE
KMKILALPYASGQLSLLVMLPDDVSGLKQLESAITSEKLIEWTSPSMME
ERKIKVYLPRMKIEEKYNLTSVLMALGITDLFSPSANLSGISSAESLK
MSQA

No. 2: N334_07249
(SEQ ID NO. 2)
IKNILQPGSVDPQTEMVLVNAVYFKGMWEKAFKDEDTQAVPFRMTEQES
KPVQMMYQIGSFKVAVMASEKIKILELPYASGELSMLVLLPDDVSGLEQ
LETAITLDKLTEWTSSNAMEERKMKVYLPRMKIEKKYNLTSVLIALGM
TDLF

No. 3: N326_09826
(SEQ ID NO. 3)
IKNILQPGSVDPQTEMILVNAIYFKGVWEKAFKDEDTQAVPFRMTEQES
KPVQMMYQFGSFKVAAMAAEKMKILELPYASGALSMLVLLPDDVSGLEQ
LESAITFEKLMEWTSSNMMEEKKIKVYLPRMKMEEKYNFTSVLMALGM
TDLF

No. 4: N309_12713
(SEQ ID NO. 4)
IRNMFLPGTVNSQSEMVLANAVSFKGMWENAFKDEDTQELPFRVSEQES
KPVQMMYQVGSFRVATLAAEKVKILELPYSSRLLSMLVLVPDSIADMEQ
LEAIISHEKLNEWTSPNVMERKTVKVYFPRMKLGEKYNLTSAFISMGMT
DVL

No. 5: SERPINB14 (EMU)
(SEQ ID NO. 5)
ITEQESKPVQMMYQAGSFKVATVAAEKMKILELPYASGELSMFVLLPDD
ISGLEQLETTISIEKLSEWTSSNMMEDRKMKVYLPHMKIEEKYNLTSVL
VALGMTDLFSPSANLSGISTAQTLKMSEAIHGAYVEIYEAGSEMATST
GVLV

No. 6: N301_12937
(SEQ ID NO. 6)
IKNILQPGSVDSQTEMVLVNAIYFKGMWEKAFKDEDTQTVPFRMTEQET
KPVQMMYQIGTFKVAVMPSEKMKILELPYASGELCMLVMLPDDVSGLEE
LESSITVEKLMEWTSSNMMEERKMKVFLPRMKIEEKYNLTSVLMALGMT
DLF

No. 7: AS28_15041
(SEQ ID NO. 7)
PVQMMYQIGSYKVAVIASEKMKILELPYASGELSMLVLLPDDVSGLEQL
ETAITFEKLMEWTSSNMMEERKVKVYLPRMKIEEKYNLTSVLMALGMTD
LFSPSANLSGISSAESLKMSEAIHEAFVEIYEAGSEVVGSTEAGMEVT
SVSE

No. 8: N334_07249
(SEQ ID NO. 8)
IKNILQPGSVDPQTEMVLVNAVYFKGMWEKAFKDEDTQAVPFRMTEQES
KPVQMMYQIGSFKVAVMASEKIKILELPYASGELSMLVLLPDDVSGLE
QLETAITLDKLTEWTSSNAMEERKMKVYLPRMKIEKKYNLTSVLIALGM
TDLF

No. 9: N332_13903
(SEQ ID NO. 9)
IKNILQPSSVNPQTEMVLVNAIYLKGMWEKAFKDEDTQTMPFRVTQQES
KPVQMMYQIGSFKVAVIASEKMKILELPYTSGQLSMLVLLPDDVSGLE
QVESAITAEKLMEWTSPSIMEERTMKVYLPRMKMVEKYNLTSVLMALGM
TDLF

No. 10: N324_12318
(SEQ ID NO. 10)
IKNILQPSSVDPQTEMVLVNAIYFKGMWQKAFKDEDTQAVPFRISEQES
KPVQMMYQIGSFKVAVMAAEKMKILELPYASGELSMLVLLPDEVSGLE
QLENAITVEKLMEWTSSSPMEERIMKVYLPRMKIEEKYNLTSVLMALGI
TDLF

-continued

No. 11: N321_14342
(SEQ ID NO. 11)
AIYFKGMWQRAFKEEDTQAVPFRISEKESKPVQMMYQIGSFKVAVIPSE

KIKILELPYASGLLSMLVILPDDVSGLEQLENAITLEKLMQWTSSNMM

EERKIKVYLPRMRMEEKYNLTSVFMALGITDLFSSSANLSGISSAESLK

MSDA

No. 12: N337-12018
(SEQ ID NO. 12)
IKNILQPGSVDSQTEMVLVNAVYFKGMWEKAFKDEDTQAMPFRMTEQES

TPVQMMYQVGSFKVAEMASEKMKILELPYASGELSMLVLLPDDVSGLE

EIENAITFEKLTEWTSSSIMEERKIKVYLPRMKMEEKYNLTSVLMALGM

TDLF

No. 13: N338-08254
(SEQ ID NO. 13)
IKNILKPSSVDSQTEMVLVNAIYFKGLWEKAFKDEDTQAMPFRITEQES

KPVQMMYQIGSFKVAEMAAEKMKILELPYASGELSMLVLLPDDVSSLE

QIETAITFEKLTEWTSSSVMEERKMKVYLPRMKMEEKYNLTSVLMALGV

TDLF

No. 14: AS27_14686
(SEQ ID NO. 14)
PVQMMYQIGSYKVAVIASEKMKILELPYASRELSMLVLLPDDVSGLEQL

ETAITFEKLMEWTSSNMMEERKVKVYLPRMKIEEKYNLTSVLMALGMT

DLFSPSANLSGISSAESLKMSEAVHEAFVEIYEAGSEVVGSTGAGMEVT

SVSE

No. 15: N327_05653
(SEQ ID NO. 15)
IKNILQPGSVDPQTEMVLVNAIYFKGMWEKAFKDEDTQAVPFRMTEQES

KTVQMMYQIGSFKVAVMASEKMKILELPYASGELSMLVMLPDDVSGLEQ

LETAITFEKLMEWTSSNMMEERKMKVYLPRMKMEEKYNLTSVLMALGVT

DLF

No. 16: Anapl_17064
(SEQ ID NO. 16)
VDSQTTMVLVNAIYFKGMWEKAFKDEDTQAMPFRMTEQESKPVQMMYQV

G
SFKVAMVTSEKMKILELPFASGMMSMFVLLPDEVSGLEQLESTISFE

KLTEWTSSTMMEERRMKVYLPRMKMEEKYNLTSVFMALGMTDLFSSSAN

MSGI

No. 17: N312_13708
(SEQ ID NO.17)
IKNILQPGSVDPQTQMVLVNAIYFKGVWEKAFKDEDTQAVPFRMTKQES

KPVQMMYQIGSFKVAVMASEKMKILELPYASGQLSMLVMLPDDVSGLE

QIENAITFEKLMEWTNPNMMEERKMKVYLPRMKMEEKYNLTSVLMALGM

TDLF

No. 18: N306_04127
(SEQ ID NO. 18)
AIYFKGMWQKAFKDEDTQEVPFRMTEQQSKPVQMMYQTGSFKVAVVASE

KMKILALPYASGQLSLLVMLPDDVSGLKQLESAITSEKLIEWTSPSMME

ERKIKVYLPRMKIEEKYNLTSVLMALGITDLFSPSANLSGISSAESLKM

SQA.

2. Transcription and Translation of Proteins

After thawing, the mixed solution of $S^{35}$-methionine and TNT SP6 is placed on ice. 40 µL of TNT mixed solution, 1 µL (1 µg/µL) of constructed plasmid, and 5 µL of $S^{35}$-methionine are sequentially added. 4 µL of nuclease-free water is used to supplement the total reaction system to 50 µL. After thorough mixing, the mixture is incubated in a 30° C. water bath for 90 minutes, and then removed and placed on ice and prepared to pass NAP-5 column.

One NAP-5 column is taken out and placed on a test tube rack, both the upper covers and lower covers are opened, and after the equilibration solution is discarded, 1 mL of TBST buffer is added to equilibrate the NAP-5 column with elution for 3 times. The reaction mixture is carefully applied to packing surface of the NAP-5 column, after washing the reaction tube with 100 µL of buffer, the reaction mixture is still added to the NAP-5 column, after the red liquid slowly moved down to the position at ⅔ of the column, 500 µL of buffer is added, the color variation of the drop under the column is carefully observed, approximately 500 µL of red column passing liquid is collected, 2 µL of column passing antigen is taken out from the column passing liquid and mixed uniformly with 1 mL of scintillation solution in the scintillation tube, and the number of pulses per minute (counts per minute, CPM) is counted on a 96 well β Counter scintillation Counter, and a value below 8000CMP is considered to be a lower transcription and translation efficiency.

3. Combination and Detection of the Sample to be Tested and Antigen

5 µL of sample serum or a simulated sample is added into each well, each sample and quality control serum are double-wells, a proper amount of marker protein is taken, the marker protein is diluted to 20000 CPM/60 µL by using 6 mL of TBST buffer solution, 60 µL of diluted marker protein is added into each well. It is required that the CPM value for each well is greater than or equal to 20000, the marker protein and the serum are uniformly mixed at the room temperature and oscillated for 1 hour, and the mixture is in a refrigerator at 4° C. overnight. PVDF plates are incubated at 150 µL TBST/well overnight in a refrigerator at 4° C. The next day, the liquid in PVDF plate is poured out, 25 µL of protein A/G mixed agarose (62.5% PA and 20% PG are prepared according to 4:1) is added into each well, 50 µL of mixed solution is sequentially taken out from each well of a 96-well well and transferred onto a 96-well PVDF filter well, after the mixed solution is uniformly mixed in a refrigerator at 4° C. for 1 hour, the antigen-antibody complex is taken out after precipitation, the liquid is pumped out by a vacuum pump, 200 µL of TBST buffer solution is firstly added into each well of the PVDF filter plate to wash the precipitate, the liquid is pumped out by a vacuum pump to leave the precipitate. 150 µL of buffer solution is added to repeatedly wash for 7 times, 60 µL of scintillation solution is added into each well after the mixture is dried by an oven, and the mixture is counted on a 96-well β Counter and each well counting for 1 minute.

The radiometric index is calculated as follows.

Radioactivity Index (Index)=(specimen serum CPM−negative quality control CPM)/(positive quality control CPM−negative quality control CPM).

All data are statistically analyzed using SPASS26 software, and all metric data that follow a normal distribution are expressed as mean±standard deviation ($\bar{x}$±s) using one-way ANOVA, ANOVA trend test and the like. $P<0.05$ is significant in difference and has statistical significance.

4. Experimental Results
4.1 Plasmid Transcription Efficiency of No. 1 to 18 Protein Scaffold to be Selected The mixed solution of $S^{35}$-methionine and TNT SP6 are thawed, and then placed on ice, 40 μL of the TNT mixed solution, 1 μL (1 μg/μL) of constructed No. 1 to 18 protein scaffold plasmid and 5 μL $S^{35}$-methionine are sequentially added. The total reaction system is supplemented with 4 μL of nuclease-free water to 50 μL, placed in a water bath box at 30° C. for incubation for 90 minutes after mixing fully and uniformly, subsequently, taken out, placed on ice, prepared to pass NAP-5 column so as to detect 2 μL transcription efficiency according to the above method.

Figure 3:
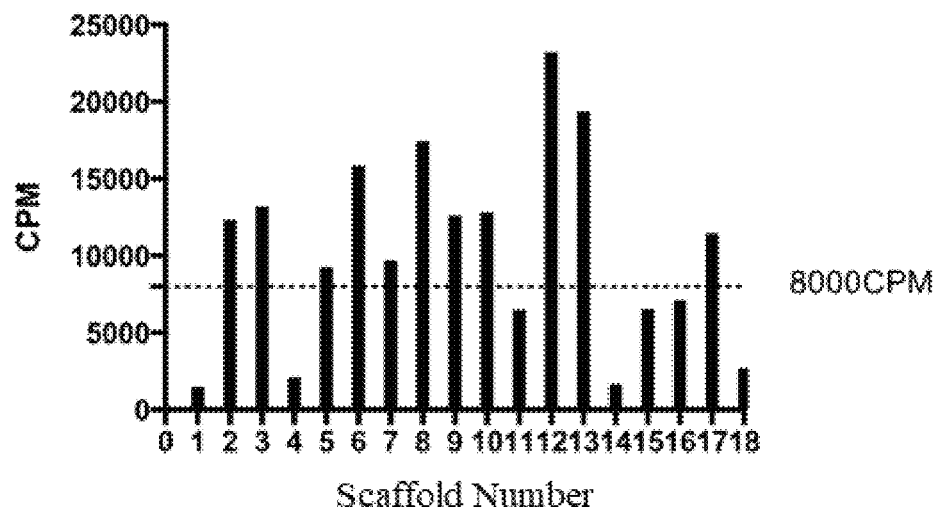

As illustrated in FIG. 3, protein scaffolds No. 1, 4, 11, 14, 15, 16, 18 are excluded because of the low transcription efficiency (<8000 CPM), which is detrimental to subsequent batch detection. The remaining scaffold proteins are used in the next experiments.

4.2 Cross-Reaction of Scaffold Proteins with Normal Persons

Because of the possible homology between the scaffold proteins and proteins in some human food, in order to avoid the non-specific binding of antibodies in human serum to the scaffold protein used in the assay caused by food allergy, the scaffold proteins that may have this problem are designed to be excluded by reacting with normal human serum. The 2, 3, 5, 6, 7, 8, 9, 10, 12, 13 and 17 scaffold proteins obtained after transcription and translation are incubated with 110 samples of normal human serum according to the above experimental procedure, washed to remove unbound antigen proteins to detect CPM values. In normal samples without cross reaction, the data distribution is relatively concentrated and the dispersion is not high. Here, the coefficient of variance of each group of samples will be calculated. When the CV<30%, it is considered that the sample dispersion is moderate and the data are relatively concentrated, and the next step can be conducted to detect the cross reaction with serum from patients with metabolic abnormalities.

TABLE 2

Coefficient of variance of reaction between scaffold proteins and normal human serum

| Scaffold Number | Mean CPM ± Standard Deviation ($\bar{x} \pm s$) | Coefficient (cv) of Variation % |
| --- | --- | --- |
| 2 | 638.73 ± 209.95 | 33 |
| 3 | 369.47 ± 84.18 | 23 |
| 5 | 263.32 ± 90.63 | 35 |
| 6 | 393.48 ± 126.27 | 32 |
| 7 | 168.70 ± 53.24 | 32 |
| 8 | 305.24 ± 116.41 | 38 |
| 9 | 342.11 ± 106.18 | 31 |
| 10 | 250.53 ± 58.92 | 24 |
| 12 | 268.97 ± 60.50 | 22 |
| 13 | 410.03 ± 129.39 | 32 |
| 17 | 597.61 ± 112.44 | 19 |

The above results show that protein scaffolds 2, 5, 6, 7, 8, 9, and 13 have significant data variation due to CV greater than 30%, and will be excluded from the next experiment.

4.3 Cross-Reaction of Scaffold Proteins with Patients with Metabolic Disease

Because the microenvironment in metabolizing patients is different from that of normal human, there may be some metabolic molecules affecting the detection on specificity, and scaffold proteins that may be disturbed by such microenvironment are further excluded herein. The 3, 10, 12, and 17 scaffold proteins obtained after transcription and translation are incubated with serum samples from non TDM130 metabolic patients according to the above experimental procedure, washed to remove unbound antigen proteins to detect CPM values. In samples without cross reaction, the data distribution is relatively concentrated and the dispersion is not high. Here, the coefficient of variance of each group of samples will be calculated. When the CV<30%, it is considered that the sample dispersion is moderate and the data are relatively concentrated, and the next step of the experiment can be conducted.

TABLE 3

Coefficient of variance of reaction between scaffold protein and metabolic patients serum

| Scaffold Number | Mean CPM ± Standard Deviation ($\bar{x} \pm s$) | Coefficient of Variance(cv)% |
| --- | --- | --- |
| 3 | 728.43 ± 253.58 | 35 |
| 10 | 673.79 ± 309.11 | 46 |
| 12 | 469.79 ± 123.36 | 26 |
| 17 | 1199.79 ± 444.27 | 37 |

The results show that protein scaffolds No. 3, 10 and 17 have CV of greater than 30%, larger data variation and relative large overall mean value, which indicates that the background is too high and the application of the protein scaffolds No. 3, 10 and 17 in the next step is eliminated. Therefore, the protein scaffolds No. 12 (R12) is selected to be applied to the subsequent experiment.

Example 2

Application of Scaffold R12 in Capturing Antibody BTN3A1A
1. Plasmid Construction Plan After the codon optimization according to the mammalian protein expression system (avoiding two enzyme cleavage sites), the plasmid is constructed on the plasmid vector pTnT™ Vector (L5610, Promega), including the kozak sequence, XhoI and XbaI enzyme cleavage sites, and the target sequence.

The plasmid structure includes: XhoI (ctcgag)+kozak sequence (gccacc)+ATG+target sequence+stop codon+XbaI.

Figure 4:
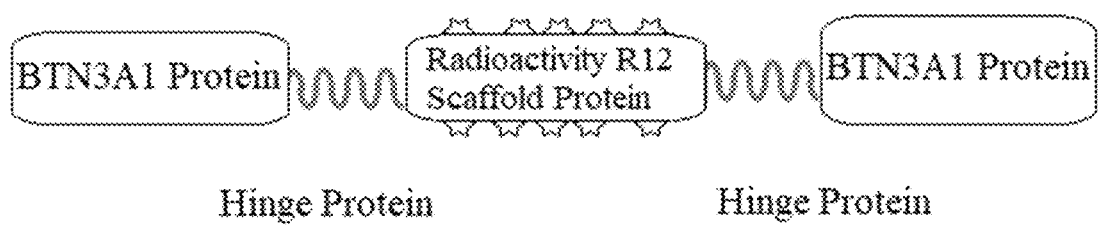

Two sections of BTN3A1 genes are connected to two ends of a No. 12 protein scaffold R12 through hinge genes, and sequences are inserted into the vectors to construct the corresponding plasmids. Each radioactive antigen protein AR12A obtained after transcription and translation includes two BTN3A1 protein antigen structure domains, the intermediate of the two BTN3A1 protein antigen structure domains is connected with each other through a hinge protein (as illustrated in FIG. 4); the ability of the radioactive antigen protein for carrying radioactive signals is effectively doubled, and the ability of the radioactive antigen protein for capturing antibodies is greatly improved by the two antigen structure domains.

The target sequence of the antigen protein AR12A is as follows (PKPSTPPGSSGGGS (SEQ ID NO:25) is the hinge sequence).

(SEQ ID NO. 19)
LLGGAGYFLWQQQEEKKTQFRKKKREQELREMAWSTMKQEQSTRV

KLLEELRWRSIQYASRGERHSAYNEWKKALFKPADVILDPKTANP

-continued

```
ILLVSEDQRSVQRAKEPQDLPDNPERFNWHYCVLGCESFISGRHY

WEVEVGDRKEWHIGVCSKNVQRKGWVKMTPENGFWTMGLTDGNKY

RTLTEPRTNLKLPKPPKKVGVFLDYETGDISFYNAVDGSHIHTFL

DVSFSEALYPVFRILTLEPTALTICPAPKPSTPPGSSGGGSIKNI

LQPGSVDSQTEMVLVNAVYFKGMWEKAFKDEDTQAMPFRMTEQES

TPVQMMYQVGSFKVAEMASEKMKILELPYASGELSMLVLLPDDVS

GLEEIENAITFEKLTEWTSSSIMEERKIKVYLPRMKMEEKYNLTS

VLMALGMTDLFPKPSTPPGSSGGGSLLGGAGYFLWQQQEEKKTQF

RKKKREQELREMAWSTMKQEQSTRVKLLEELRWRSIQYASRGERH

SAYNEWKKALFKPADVILDPKTANPILLVSEDQRSVQRAKEPQDL

PDNPERFNWHYCVLGCESFISGRHYWEVEVGDRKEWHIGVCSKNV

QRKGWVKMTPENGFWTMGLTDGNKYRTLTEPRTNLKLPKPPKKVG

VFLDYETGDISFYNAVDGSHIHTFLDVSFSEALYPVFRILTLEPT

ALTICPA.
```

2. Transcription and Translation of Proteins

After thawing, the mixed solution of $S^{35}$-methionine and TNT SP6 is placed on ice, 40 μL of TNT mixed solution, 1 μL (1 μg/μl) constructed plasmid and 5 μL $S^{35}$-methionine are sequentially added. 4 μL of nuclease-free water is used to supplement the total reaction system to 50 μL. After thorough mixing, the mixture is incubated in a 30° C. water bath for 90 minutes, and then removed and placed on ice and prepared to pass NAP-5 column.

One NAP-5 column is taken out and placed on a test tube rack, both the upper covers and lower covers are opened, and after the equilibration solution is discarded, 1 mL of TBST buffer is added to equilibrate the NAP-5 column with elution for 3 times. The reaction mixture is carefully applied to packing surface of the NAP-5 column, after washing the reaction tube with 100 μL of buffer, the reaction mixture is still added to the NAP-5 column, after the red liquid was slowly moved down to the position at ⅔ of the column, 500 μL of buffer is added, the color variation of the drop under the column is carefully observed, approximately 500 μL of red column passing liquid is collected, 2 μL of column passing antigen is taken out from the column passing liquid and mixed uniformly with 1 mL of scintillation solution in the scintillation tube, and the number of pulses per minute (counts per minute, CPM) is counted on a 96 well B Counter scintillation Counter, and a value below 8000CMP is considered to be a lower transcription and translation efficiency.

3. Combination and Detection of the Sample to be Tested and Antigen

5 μL of sample serum or a simulated sample is added into each well, each sample and quality control serum are double-wells, a proper amount of marked antigen is taken, the marked antigen is diluted to 20000 CPM/60 μL by using 6 mL of TBST buffer solution, 60 μL of diluted marked antigen is added to each well. It is required that the CPM value for each well is greater than or equal to 20000, the marked antigen and the serum are uniformly mixed at the room temperature and oscillated for 1 hour, and the mixture is in a refrigerator at 4° C. overnight. PVDF plates are incubated at 150 μL TBST/well overnight in a refrigerator at 4° C. The next day, the liquid in PVDF plate is poured out, 25 μL of protein A/G mixed agarose (62.5% PA and 20% PG are prepared according to 4:1) is added into each well e, 50 μL of mixed solution is sequentially taken out from each well of a 96-well plate and transferred onto a 96-well PVDF filter plate, after the mixed solution is uniformly mixed in a refrigerator at 4° C. for 1 hour, the antigen-antibody complex is taken out after precipitation, the liquid is pumped out by a vacuum pump, 200 μL of TBST buffer solution is firstly added into each well of the PVDF filter plate to wash the precipitate, the liquid is pumped out by a vacuum pump to leave the precipitate, 150 μL of buffer solution is added to repeatedly wash for 7 times, 60 μL of scintillation solution is added into each well after the mixture is dried by an oven, and the mixture is counted on a 96-well β Counter and each well counting for 1 minute.

The radiometric index is calculated as follows.

Radioactivity Index (Index)=(specimen serum CPM−negative quality control CPM)/(positive quality control CPM−negative quality control CPM).

All data are statistically analyzed using SPASS26 software, and all metric data that follow a normal distribution are expressed as mean±standard deviation ($\bar{x}$±s) using one-way ANOVA, ANOVA trend test and the like. $P<0.05$ is significant in difference and has statistical significance.

4. Experimental Results 4.1 Determination on the Effectiveness that the Radioactive Antigen Protein AR12A Captures Antibody BTN3A1A The AR12A plasmid is transcribed and translated to obtain the corresponding antigen AR12A with radioactive signals. The corresponding commercial antibody BTN3A1A purchased is used as a simulated sample, the transcribed and translated radioactive AR12A antigen is used to capture. The radiation readings at the different simulated sample sizes are detected according to the experimental method described above.

Figure 5:
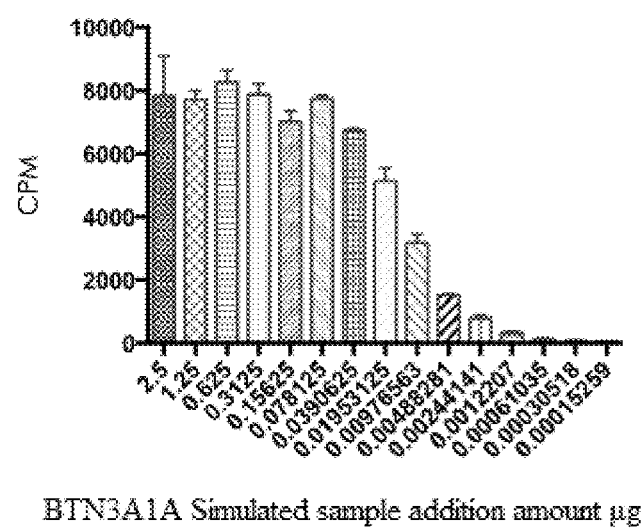

As illustrated in FIG. 5, the BTN3A1A radioactivity reading CPM decreases with decreasing simulated sample loading. After the analysis of variance trend test, $P<0.0001$, the trend is extremely significant. Thus, the transcribed and translated antigen AR12A has biological activity and can effectively capture the antibody, and the carried radioactive signal varies along with the variation of the content of the antibody.

In the subsequent experiments, the purchased antibody is used as a positive reference, and according to the signal to noise ratio (S/N)>15 (S/N: CPM value for different antibody addition amounts/CPM value for negative reference) and cost comprehensive consideration, 0.6 ug of RPS26A antibody and CPM approximately 5178 are selected as the addition amount of the positive reference, as shown in Table 3. 0.078 ug of antibody BTN3A1A, CPM approximately 7744 is used as a load for positive reference as shown in Table 4.

TABLE 4

Signal-to-noise ratio (S/N) at different RPS26A additions

| | RPS26A additive Amount (ug) | | | | | | | | | | | negative reference |
|---|---|---|---|---|---|---|---|---|---|---|---|---|
| | 2.4 | 1.2 | 0.6 | 0.3 | 0.15 | 0.075 | 0.0375 | 0.01875 | 0.009375 | 0.0046875 | 0.00234375 | |
| CPM | 5901 | 5527 | 5178 | 4614 | 4253 | 2341 | 1343 | 714 | 474 | 220 | 144 | 143 |
| (Signal to Noise Ratio) S/N | 41.27 | 38.65 | 36.21 | 32.27 | 29.74 | 16.37 | 9.39 | 4.99 | 3.31 | 1.54 | 1.01 | 1 |

Figure 6:
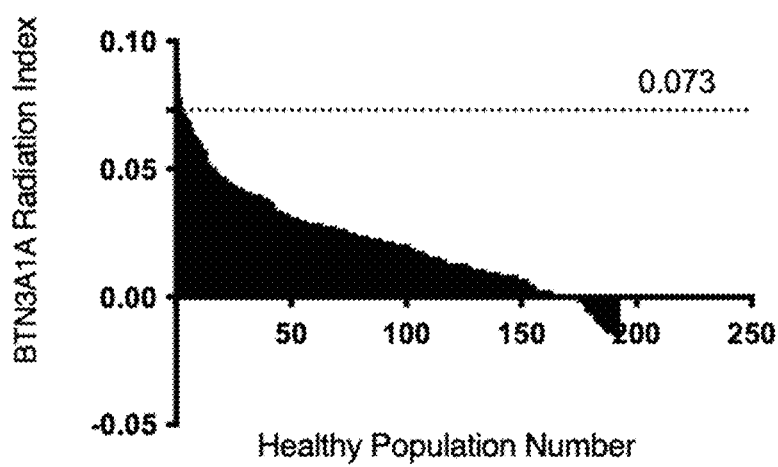
FIG. 6 illustrates a RBA BTN3 A1A threshold determination result for healthy population.

4.2 RBA Detection of BTN3A1A for Determining the Threshold Value of Healthy Population Serums of 192 healthy population are taken for detecting BTN3A1A by a radioligand binding assay method, a radioactive index is calculated, 99% percentile is taken as a threshold value. RBA BTN3A1A positive threshold value is calculated to be 0.073, and positive determination standard is greater than or equal to 0.073, as illustrated in FIG. 6.

4.3 RBA Detection of Intra Batch and Inter Batch Differences in BTN3A1A

According to the low, medium, and high BTN3A1A indexes, three serum samples are selected for repeated testing within and between batches five times each (n=5), and the coefficient of variance (CV) of intra batch and inter batch are determined. The results show that the intra batch CV of RBA BTN3A1A detection index is in the range from 4.60% to 8.58%, and the inter batch CV is in the range from 7.63% to 10.08%. A repeatability based on the positive and negative results is determined to be 100%. The results are as shown in Table 5.

TABLE 5

RBA detection of intra-batch difference and inter-batch difference of BTN3A1A

| Sample | BTN3A1A Radioactive index ($\bar{x} \pm s$) | BTN3A1A CV (%) |
|---|---|---|
| Intra-batch (n = 5) | | |
| Low value | 0.2182 ± 0.0182 | 8.35% |
| Median value | 0.4027 ± 0.0346 | 8.58% |
| High value | 1.0442 ± 0.0480 | 4.60% |
| Inter-batch (n = 5) | | |
| Low value | 0.2016 ± 0.0203 | 10.08% |
| Median value | 0.4166 ± 0.0408 | 9.78% |
| High value | 1.0231 ± 0.0781 | 7.63% |

4.4BTN3A1A Distribution Among Various Populations

Figure 7:
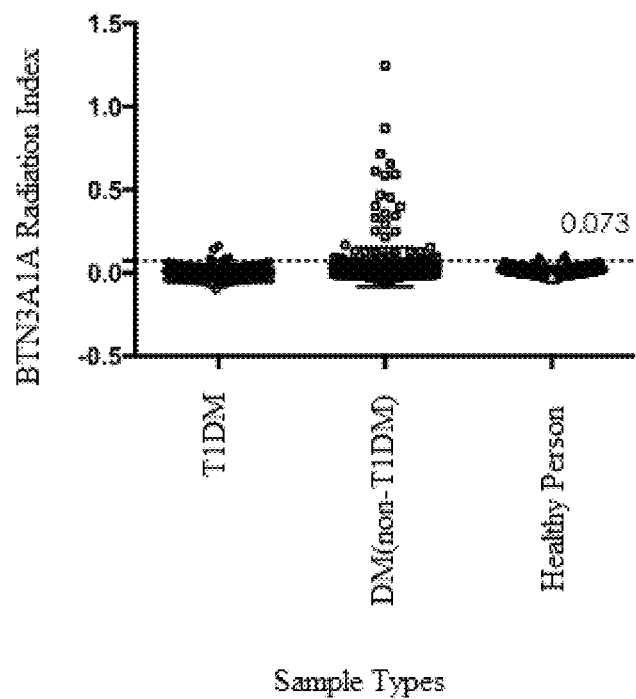
FIG. 7 illustrates distributions of BTN3A1A in T1DM patients, DM (non-T1DM) patients, and healthy population.

The percentage of BTN3A1A in T1DM, DM (non-T1DM) and healthy population are 2.17% (7/323), 9.16% (37/404) and 1.05% (2/190), respectively, and the difference is obvious through a single factor variance analysis P<0.01, which is as illustrated in FIG. 7.

4.4 Competitive Inhibition of 4.4BTN3A1A Positive Samples

Figure 8:
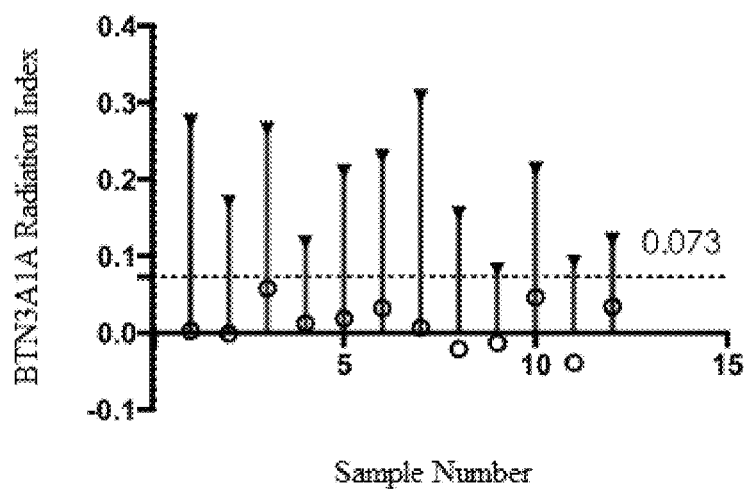
FIG. 8 illustrates an experimental result of a competitive inhibition for a RBABTN3A1A detection.

12 Cases of BTN3A1A positive samples are taken and the corresponding 2 μg of commercial BTN3A1 protein purchased without radioactive signal is added to each well in the assay for competitive inhibition experiments. As illustrated in FIG. 8, the radioactivity of the antibody is reduced to the negative range after adding BTN3A1 protein. Thus RBA BTN3A1A detection can effectively recognize the real BTN3A1A antibodies.

It can be known from the above results that the protein scaffold Ruber 12 designed in the present disclosure can effectively carry radioactive signals. The detection of BTN3A1A by RBA method is successfully established with the help of Ruber.

What is claimed is:

1. A detection kit for an anti-butyrophilin 3A1 antibody, comprising:

a radioactive antigen protein AR12A, wherein the radioactive antigen protein AR12A is obtained by labelling the antigen protein AR12A with $S^{35}$-methionine, and an amino acid sequence of the antigen protein AR12A comprises an amino acid sequence of a protein scaffold and an amino acid sequence of the BTN3A1;

the amino acid sequence of the protein scaffold is as follows:

(SEQ ID NO: 12)
IKNILQPGSVDSQTEMVLVNAVYFKGMWEKAFKDEDTQAMPFRMTEQES

TPVQMMYQVGSFKVAEMASEKMKILELPYASGELSMLVLLPDDVSGLEE

IENAITFEKLTEWTSSSIMEERKIKVYLPRMKMEEKYNLTSVLMALGMT

DLF;

the amino acid sequence of the antigen protein AR12A is as follows:

(SEQ ID NO: 19)
LLGGAGYFLWQQQEEKKTQFRKKKREQELREMAWSTMKQEQSTRVKLLE

ELRWRSIQYASRGERHSAYNEWKKALFKPADVILDPKTANPILLVSEDQ

RSVQRAKEPQDLPDNPERFNWHYCVLGCESFISGRHYWEVEVGDRKEWH

IGVCSKNVQRKGWVKMTPENGFWTMGLTDGNKYRTLTEPRTNLKLPKPP

KKVGVFLDYETGDISFYNAVDGSHIHTFLDVSFSEALYPVFRILTLEPT

ALTICPAPKPSTPPGSSGGGSIKNILQPGSVDSQTEMVLVNAVYFKGMW

EKAFKDEDTQAMPFRMTEQESTPVQMMYQVGSFKVAEMASEKMKILELP

YASGELSMLVLLPDDVSGLEEIENAITFEKLTEWTSSSIMEERKIKVYL

PRMKMEEKYNLTSVLMALGMTDLFPKPSTPPGSSGGGSLLGGAGYFLWQ

QQEEKKTQFRKKKREQELREMAWSTMKQEQSTRVKLLEELRWRSIQYAS

RGERHSAYNEWKKALFKPADVILDPKTANPILLVSEDQRSVQRAKEPQD

LPDNPERFNWHYCVLGCESFISGRHYWEVEVGDRKEWHIGVCSKNVQRK

GWVKMTPENGFWTMGLTDGNKYRTLTEPRTNLKLPKPPKKVGVFLDYET

GDISFYNAVDGSHIHTFLDVSFSEALYPVFRILTLEPTALTICPA.

2. The detection kit according to claim 1, further comprising: a Tris-Buffered Saline solution, a protein A agarose, a protein G agarose, a positive control and a negative control.

* * * * *

```
                      SEQUENCE LISTING

Sequence total quantity: 25
SEQ ID NO: 1           moltype = AA  length = 150
FEATURE                Location/Qualifiers
source                 1..150
                       mol_type = protein
                       organism = synthetic construct
SEQUENCE: 1
AIYFKGMWQK AFKDEDTQEV PFRMTEQQSK PVQMMYQTGS FKVAVVASEK MKILALPYAS  60
GQLSLLVMLP DDVSGLKQLE SAITSEKLIE WTSPSMMEER KIKVYLPRMK IEEKYNLTSV 120
LMALGITDLF SPSANLSGIS SAESLKMSQA                                 150

SEQ ID NO: 2           moltype = AA  length = 150
FEATURE                Location/Qualifiers
source                 1..150
                       mol_type = protein
                       organism = synthetic construct
SEQUENCE: 2
IKNILQPGSV DPQTEMVLVN AVYFKGMWEK AFKDEDTQAV PFRMTEQESK PVQMMYQIGS  60
FKVAVMASEK IKILELPYAS GELSMLVLLP DDVSGLEQLE TAITLDKLTE WTSSNAMEER 120
```

```
KMKVYLPRMK IEKKYNLTSV LIALGMTDLF                                    150

SEQ ID NO: 3              moltype = AA  length = 150
FEATURE                   Location/Qualifiers
source                    1..150
                          mol_type = protein
                          organism = synthetic construct
SEQUENCE: 3
IKNILQPGSV DPQTEMILVN AIYFKGVWEK AFKDEDTQAV PFRMTEQESK PVQMMYQFGS     60
FKVAAMAAEK MKILELPYAS GALSMLVLLP DDVSGLEQLE SAITFEKLME WTSSNMMEEK    120
KIKVYLPRMK MEEKYNFTSV LMALGMTDLF                                    150

SEQ ID NO: 4              moltype = AA  length = 150
FEATURE                   Location/Qualifiers
source                    1..150
                          mol_type = protein
                          organism = synthetic construct
SEQUENCE: 4
IRNMFLPGTV NSQSEMVLAN AVSFKGMWEN AFKDEDTQEL PFRVSEQESK PVQMMYQVGS     60
FRVATLAAEK VKILELPYSS RLLSMLVLVP DSIADMEQLE AIISHEKLNE WTSPNVMERK    120
TVKVYFPRMK LGEKYNLTSA FISMGMTDVL                                    150

SEQ ID NO: 5              moltype = AA  length = 150
FEATURE                   Location/Qualifiers
source                    1..150
                          mol_type = protein
                          organism = synthetic construct
SEQUENCE: 5
ITEQESKPVQ MMYQAGSFKV ATVAAEKMKI LELPYASGEL SMFVLLPDDI SGLEQLETTI     60
SIEKLSEWTS SNMMEDRKMK VYLPHMKIEE KYNLTSVLVA LGMTDLFSPS ANLSGISTAQ    120
TLKMSEAIHG AYVEIYEAGS EMATSTGVLV                                    150

SEQ ID NO: 6              moltype = AA  length = 150
FEATURE                   Location/Qualifiers
source                    1..150
                          mol_type = protein
                          organism = synthetic construct
SEQUENCE: 6
IKNILQPGSV DSQTEMVLVN AIYFKGMWEK AFKDEDTQTV PFRMTEQETK PVQMMYQIGT     60
FKVAVMPSEK MKILELPYAS GELCMLVMLP DDVSGLEELE SSITVEKLME WTSSNMMEER    120
KMKVFLPRMK IEEKYNLTSV LMALGMTDLF                                    150

SEQ ID NO: 7              moltype = AA  length = 150
FEATURE                   Location/Qualifiers
source                    1..150
                          mol_type = protein
                          organism = synthetic construct
SEQUENCE: 7
PVQMMYQIGS YKVAVIASEK MKILELPYAS GELSMLVLLP DDVSGLEQLE TAITFEKLME     60
WTSSNMMEER KVKVYLPRMK IEEKYNLTSV LMALGMTDLF SPSANLSGIS SAESLKMSEA    120
IHEAFVEIYE AGSEVVGSTE AGMEVTSVSE                                    150

SEQ ID NO: 8              moltype = AA  length = 150
FEATURE                   Location/Qualifiers
source                    1..150
                          mol_type = protein
                          organism = synthetic construct
SEQUENCE: 8
IKNILQPGSV DPQTEMVLVN AVYFKGMWEK AFKDEDTQAV PFRMTEQESK PVQMMYQIGS     60
FKVAVMASEK IKILELPYAS GELSMLVLLP DDVSGLEQLE TAITLDKLTE WTSSNAMEER    120
KMKVYLPRMK IEKKYNLTSV LIALGMTDLF                                    150

SEQ ID NO: 9              moltype = AA  length = 150
FEATURE                   Location/Qualifiers
source                    1..150
                          mol_type = protein
                          organism = synthetic construct
SEQUENCE: 9
IKNILQPSSV NPQTEMVLVN AIYLKGMWEK AFKDEDTQTM PFRVTQQESK PVQMMYQIGS     60
FKVAVIASEK MKILELPYTS GQLSMLVLLP DDVSGLEQVE SAITAEKLME WTSPSIMEER    120
TMKVYLPRMK MVEKYNLTSV LMALGMTDLF                                    150

SEQ ID NO: 10             moltype = AA  length = 150
FEATURE                   Location/Qualifiers
source                    1..150
                          mol_type = protein
                          organism = synthetic construct
SEQUENCE: 10
IKNILQPSSV DPQTEMVLVN AIYFKGMWQK AFKDEDTQAV PFRISEQESK PVQMMYQIGS     60
```

```
FKVAVMAAEK MKILELPYAS GELSMLVLLP DEVSGLEQLE NAITVEKLME WTSSSPMEER    120
IMKVYLPRMK IEEKYNLTSV LMALGITDLF                                    150

SEQ ID NO: 11           moltype = AA  length = 150
FEATURE                 Location/Qualifiers
source                  1..150
                        mol_type = protein
                        organism = synthetic construct
SEQUENCE: 11
AIYFKGMWQR AFKEEDTQAV PFRISEKESK PVQMMYQIGS FKVAVIPSEK IKILELPYAS    60
GLLSMLVILP DDVSGLEQLE NAITLEKLMQ WTSSNMMEER KIKVYLPRMR MEEKYNLTSV    120
FMALGITDLF SSSANLSGIS SAESLKMSDA                                    150

SEQ ID NO: 12           moltype = AA  length = 150
FEATURE                 Location/Qualifiers
source                  1..150
                        mol_type = protein
                        organism = synthetic construct
SEQUENCE: 12
IKNILQPGSV DSQTEMVLVN AVYFKGMWEK AFKDEDTQAM PFRMTEQEST PVQMMYQVGS    60
FKVAEMASEK MKILELPYAS GELSMLVLLP DDVSGLEEIE NAITFEKLTE WTSSSIMEER    120
KIKVYLPRMK MEEKYNLTSV LMALGMTDLF                                    150

SEQ ID NO: 13           moltype = AA  length = 150
FEATURE                 Location/Qualifiers
source                  1..150
                        mol_type = protein
                        organism = synthetic construct
SEQUENCE: 13
IKNILKPSSV DSQTEMVLVN AIYFKGLWEK AFKDEDTQAM PFRITEQESK PVQMMYQIGS    60
FKVAEMAAEK MKILELPYAS GELSMLVLLP DDVSSLEQIE TAITFEKLTE WTSSSVMEER    120
KMKVYLPRMK MEEKYNLTSV LMALGVTDLF                                    150

SEQ ID NO: 14           moltype = AA  length = 150
FEATURE                 Location/Qualifiers
source                  1..150
                        mol_type = protein
                        organism = synthetic construct
SEQUENCE: 14
PVQMMYQIGS YKVAVIASEK MKILELPYAS RELSMLVLLP DDVSGLEQLE TAITFEKLME    60
WTSSNMMEER KVKVYLPRMK IEEKYNLTSV LMALGMTDLF SPSANLSGIS SAESLKMSEA    120
VHEAFVEIYE AGSEVVGSTG AGMEVTSVSE                                    150

SEQ ID NO: 15           moltype = AA  length = 150
FEATURE                 Location/Qualifiers
source                  1..150
                        mol_type = protein
                        organism = synthetic construct
SEQUENCE: 15
IKNILQPGSV DPQTEMVLVN AIYFKGMWEK AFKDEDTQAV PFRMTEQESK TVQMMYQIGS    60
FKVAVMASEK MKILELPYAS GELSMLVMLP DDVSGLEQLE TAITFEKLME WTSSNMMEER    120
KMKVYLPRMK MEEKYNLTSV LMALGVTDLF                                    150

SEQ ID NO: 16           moltype = AA  length = 150
FEATURE                 Location/Qualifiers
source                  1..150
                        mol_type = protein
                        organism = synthetic construct
SEQUENCE: 16
VDSQTTMVLV NAIYFKGMWE KAFKDEDTQA MPFRMTEQES KPVQMMYQVG SFKVAMVTSE    60
KMKILELPFA SGMMSMFVLL PDEVSGLEQL ESTISFEKLT EWTSSTMMEE RRMKVYLPRM    120
KMEEKYNLTS VFMALGMTDL FSSSANMSGI                                    150

SEQ ID NO: 17           moltype = AA  length = 150
FEATURE                 Location/Qualifiers
source                  1..150
                        mol_type = protein
                        organism = synthetic construct
SEQUENCE: 17
IKNILQPGSV DPQTQMVLVN AIYFKGVWEK AFKDEDTQAV PFRMTKQESK PVQMMYQIGS    60
FKVAVMASEK MKILELPYAS GQLSMLVMLP DDVSGLEQIE NAITFEKLME WTNPNMMEER    120
KMKVYLPRMK MEEKYNLTSV LMALGMTDLF                                    150

SEQ ID NO: 18           moltype = AA  length = 150
FEATURE                 Location/Qualifiers
source                  1..150
                        mol_type = protein
                        organism = synthetic construct
SEQUENCE: 18
```

```
                                                        -continued

AIYFKGMWQK AFKDEDTQEV PFRMTEQQSK PVQMMYQTGS FKVAVVASEK MKILALPYAS   60
GQLSLLVMLP DDVSGLKQLE SAITSEKLIE WTSPSMMEER KIKVYLPRMK IEEKYNLTSV  120
LMALGITDLF SPSANLSGIS SAESLKMSQA                                   150

SEQ ID NO: 19              moltype = AA  length = 682
FEATURE                    Location/Qualifiers
source                     1..682
                           mol_type = protein
                           organism = synthetic construct
SEQUENCE: 19
LLGGAGYFLW QQQEEKKTQF RKKKREQELR EMAWSTMKQE QSTRVKLLEE LRWRSIQYAS   60
RGERHSAYNE WKKALFKPAD VILDPKTANP ILLVSEDQRS VQRAKEPQDL PDNPERFNWH  120
YCVLGCESFI SGRHYWEVEV GDRKEWHIGV CSKNVQRKGW VKMTPENGFW TMGLTDGNKY  180
RTLTEPRTNL KLPKPPKKVG VFLDYETGDI SFYNAVDGSH IHTFLDVSFS EALYPVFRIL  240
TLEPTALTIC PAPKPSTPPG SSGGGSIKNI LQPGSVDSQT EMVLVNAVYF KGMWEKAFKD  300
EDTQAMPFRM TEQESTPVQM MYQVGSFKVA EMASEKMKIL ELPYASGELS MLVLLPDDVS  360
GLEEIENAIT FEKLTEWTSS SIMEERKIKV YLPRMKMEEK YNLTSVLMAL GMTDLFPKPS  420
TPPGSSGGGS LLGGAGYFLW QQQEEKKTQF RKKKREQELR EMAWSTMKQE QSTRVKLLEE  480
LRWRSIQYAS RGERHSAYNE WKKALFKPAD VILDPKTANP ILLVSEDQRS VQRAKEPQDL  540
PDNPERFNWH YCVLGCESFI SGRHYWEVEV GDRKEWHIGV CSKNVQRKGW VKMTPENGFW  600
TMGLTDGNKY RTLTEPRTNL KLPKPPKKVG VFLDYETGDI SFYNAVDGSH IHTFLDVSFS  660
EALYPVFRIL TLEPTALTIC PA                                          682

SEQ ID NO: 20              moltype = AA  length = 9
FEATURE                    Location/Qualifiers
source                     1..9
                           mol_type = protein
                           organism = synthetic construct
SEQUENCE: 20
ALAGTLPVL                                                            9

SEQ ID NO: 21              moltype = AA  length = 9
FEATURE                    Location/Qualifiers
source                     1..9
                           mol_type = protein
                           organism = synthetic construct
SEQUENCE: 21
KMASFLAFL                                                            9

SEQ ID NO: 22              moltype = AA  length = 9
FEATURE                    Location/Qualifiers
source                     1..9
                           mol_type = protein
                           organism = synthetic construct
SEQUENCE: 22
GLYAVAASV                                                            9

SEQ ID NO: 23              moltype = AA  length = 9
FEATURE                    Location/Qualifiers
source                     1..9
                           mol_type = protein
                           organism = synthetic construct
SEQUENCE: 23
FLDVSFSEA                                                            9

SEQ ID NO: 24              moltype = AA  length = 9
FEATURE                    Location/Qualifiers
source                     1..9
                           mol_type = protein
                           organism = synthetic construct
SEQUENCE: 24
KLPKPPKKV                                                            9

SEQ ID NO: 25              moltype = AA  length = 14
FEATURE                    Location/Qualifiers
source                     1..14
                           mol_type = protein
                           organism = synthetic construct
SEQUENCE: 25
PKPSTPPGSS GGGS                                                     14
```